(12) United States Patent
Woodbridge

(10) Patent No.: US 8,226,899 B2
(45) Date of Patent: Jul. 24, 2012

(54) APPARATUS AND METHOD FOR SANITIZING AIR AND SPACES

(76) Inventor: Terrance O. Woodbridge, Cary, NC (US)

( * ) Notice: Subject to any disclaimer, the term of this patent is extended or adjusted under 35 U.S.C. 154(b) by 430 days.

(21) Appl. No.: 12/453,276

(22) Filed: May 5, 2009

(65) Prior Publication Data
US 2010/0196215 A1    Aug. 5, 2010

Related U.S. Application Data

(63) Continuation-in-part of application No. 11/289,363, filed on Nov. 30, 2005.

(60) Provisional application No. 61/071,530, filed on May 5, 2008.

(51) Int. Cl.
*B01J 19/08* (2006.01)

(52) U.S. Cl. ............... 422/186.04; 422/186.3; 422/121

(58) Field of Classification Search ............ 422/186.04, 422/186.3, 121
See application file for complete search history.

(56) References Cited

U.S. PATENT DOCUMENTS

| | | |
|---|---|---|
| 906,468 A | 12/1908 | Steynis |
| 1,157,859 A | 10/1915 | Freet |
| 1,454,219 A | 5/1923 | Goedicke |
| 1,505,669 A | 8/1924 | Quain |
| 2,687,781 A * | 8/1954 | Sens ........................... 55/514 |
| 2,778,443 A | 1/1957 | Yereance |
| 3,730,874 A | 5/1973 | Trub |
| 3,833,492 A | 9/1974 | Bollyky |
| 3,921,002 A | 11/1975 | Williams et al. |
| 3,967,131 A | 6/1976 | Slipiec |
| 4,025,441 A | 5/1977 | Tabata et al. |
| 4,048,668 A | 9/1977 | Von Bargen et al. |
| 4,049,552 A | 9/1977 | Arff |
| 4,051,045 A | 9/1977 | Yamamoto et al. |
| 4,079,260 A | 3/1978 | Dmitriev et al. |
| 4,101,783 A | 7/1978 | Hutter |
| 4,123,664 A | 10/1978 | Yamamura et al. |
| 4,128,768 A | 12/1978 | Yamamoto et al. |
| 4,159,971 A | 7/1979 | Gneupel |
| 4,216,096 A | 8/1980 | Pare et al. |
| 4,234,800 A | 11/1980 | Kenly et al. |
| 4,323,379 A * | 4/1982 | Shearin ........................... 55/511 |
| 4,383,976 A | 5/1983 | Notaro |
| 4,411,756 A | 10/1983 | Bennett et al. |
| 4,417,966 A | 11/1983 | Krauss et al. |
| 4,461,744 A | 7/1984 | Erni et al. |

(Continued)

FOREIGN PATENT DOCUMENTS

CN    1312448 A    9/2001

(Continued)

OTHER PUBLICATIONS

Supplemental European Search Report dated Oct. 4, 2010.

(Continued)

*Primary Examiner* — Kishor Mayekar
(74) *Attorney, Agent, or Firm* — McGinn IP Law Group, PLLC

(57) ABSTRACT

An in-duct apparatus for sanitizing air includes a reaction unit, configured to be mounted in an air duct, for generating reactive oxygen species from oxygen in air received in the reaction unit to be sanitized. Airborne contaminants in the received air are substantially neutralized by the generated reactive oxygen species before the air is discharged from the reaction unit.

4 Claims, 12 Drawing Sheets

U.S. PATENT DOCUMENTS

| | | | |
|---|---|---|---|
| 4,504,446 A | 3/1985 | Kunicki et al. | |
| 4,614,573 A | 9/1986 | Masuda | |
| 4,640,782 A | 2/1987 | Burleson | |
| 4,650,573 A | 3/1987 | Nathanson | |
| 4,656,010 A | 4/1987 | Leitzke et al. | |
| 4,690,803 A | 9/1987 | Hirth | |
| 4,696,800 A | 9/1987 | Sasaki et al. | |
| 4,725,412 A | 2/1988 | Ito | |
| 4,764,349 A | 8/1988 | Arff et al. | |
| 4,877,588 A | 10/1989 | Ditzler et al. | |
| 4,886,645 A | 12/1989 | Fischer et al. | |
| 4,960,569 A | 10/1990 | Fovell et al. | |
| 4,981,656 A | 1/1991 | Leitzke | |
| 5,004,587 A | 4/1991 | Tacchi | |
| 5,008,087 A | 4/1991 | Batchelor | |
| 5,034,198 A | 7/1991 | Kaiga et al. | |
| 5,093,087 A | 3/1992 | Freeman | |
| 5,124,132 A | 6/1992 | Francis, Jr. et al. | |
| 5,145,653 A | 9/1992 | Fischer et al. | |
| 5,268,151 A | 12/1993 | Reed et al. | |
| 5,387,842 A | 2/1995 | Roth et al. | |
| 5,411,713 A | 5/1995 | Iwanaga | |
| 5,508,008 A | 4/1996 | Wasser | |
| 5,833,740 A * | 11/1998 | Brais | 96/16 |
| 5,989,303 A * | 11/1999 | Hodge | 55/486 |
| 6,066,348 A | 5/2000 | Yuan et al. | |
| 6,165,423 A | 12/2000 | Crosbie | |
| 6,228,149 B1 | 5/2001 | Alenichev et al. | |
| 6,280,691 B1 | 8/2001 | Homeyer et al. | |
| 6,481,219 B2 | 11/2002 | Palermo | |
| 6,503,547 B1 | 1/2003 | Lima | |
| 6,528,023 B2 | 3/2003 | Fleischer | |
| 6,613,277 B1 * | 9/2003 | Monagan | 422/24 |
| 6,620,385 B2 | 9/2003 | Fujii | |
| 6,811,757 B2 | 11/2004 | Niv et al. | |
| 6,866,828 B2 | 3/2005 | Segawa et al. | |
| 6,893,610 B1 | 5/2005 | Barnes | |
| 6,991,768 B2 | 1/2006 | Keras et al. | |
| 7,651,555 B2 * | 1/2010 | Roseberry et al. | 96/223 |
| 2003/0066285 A1 | 4/2003 | Raybone et al. | |
| 2003/0121770 A1 | 7/2003 | McNulty, Jr. | |
| 2004/0175318 A1 | 9/2004 | Segawa et al. | |
| 2004/0184972 A1 * | 9/2004 | Kelly et al. | 422/186.04 |
| 2004/0262241 A1 | 12/2004 | Socha | |
| 2005/0023128 A1 | 2/2005 | Keras et al. | |
| 2005/0169821 A1 | 8/2005 | Boschert et al. | |
| 2005/0186108 A1 | 8/2005 | Fields | |

FOREIGN PATENT DOCUMENTS

| | | |
|---|---|---|
| DE | 1923 081 | 11/1970 |
| EP | 0 560 690 | 9/1993 |
| EP | 1 125 588 A2 | 2/2001 |
| EP | 1 508 289 | 2/2005 |
| JP | 10-511572 | 11/1998 |
| JP | 10-314289 | 12/1998 |
| JP | 2001-221565 | 8/2001 |
| JP | 2005-95649 | 4/2005 |
| WO | 96/20017 | 7/1996 |
| WO | WO 00/78670 A1 | 12/2000 |
| WO | 03/038351 | 5/2003 |
| WO | 03/092752 | 11/2003 |
| WO | 03/101498 | 12/2003 |

OTHER PUBLICATIONS

European Search Opinion dated Oct. 4, 2010.
Office Action dated Jun. 22, 2010 in U.S. Appl. No. 11/289,363.
Chinese Office Action dated May 26, 2011, with English translation.
Japanese Office Action dated Mar. 21, 2012, with English translation.
International Preliminary Report on Patentability dated Feb. 8, 2012.

* cited by examiner

APPARATUS AND METHOD FOR SANITIZING AIR AND SPACES

CROSS REFERENCE TO RELATED APPLICATIONS

The present application is a continuation-in-part application of co-pending U.S. patent application Ser. No. 11/289,363 filed on Nov. 30, 2005, which is incorporated, in its entirety, herein by reference. Furthermore, the present application relates to U.S. provisional Patent Application Ser. No. 61/071,530, filed May 5, 2008 to Terrance Woodbridge, entitled "IN DUCT UNIT", which is incorporated, in its entirety, herein by reference.

FIELD OF THE INVENTION

The present invention relates to a method and apparatus for sanitizing air and spaces through the generation of reactive oxygen species. More particularly, the present invention relates to an apparatus for sanitizing air and spaces, the apparatus being mountable in an air duct.

BACKGROUND OF THE INVENTION

Temperature changes and changes in the moisture in the air feeding into heating, ventilation, and air-conditioning (HVAC) systems increases the number of micro-organisms in the air, producing increased colonies of certain fungi, viruses, and bacteria, all of which are potentially harmful. Additionally, dirty air ducts and dirty HVAC system components can similarly increase the number of micro-organisms in the air, producing increased colonies of certain fungi, viruses, and bacteria.

HVAC systems in residences, office buildings, as well as hospitals, can be a source of various pathogens, which spread infectious micro-organisms from one zone to another—a principal cause of Sick Building Syndrome, recognized by the World Health Organization as a threat to healthy work and living environments.

The purification of environments can be achieved using reactive oxygen species, including ozone. Ozone has been used to purify air conditioning systems in buildings and to sanitize warehouses where products are stored. Despite its widespread use, this basic technique has the disadvantage of accumulating more ozone than is necessary in the treated environment, requiring the elimination of the excess ozone. Several different improvements in this method have been made in an attempt to control the levels of ozone in the environment being treated.

One such improvement provides high initial levels of ozone to the environment sufficient to produce the desired bacteriostatic or bacteriocidal effect. Later the levels of ozone are reduced so that they do not produce harmful effects to the products being treated or to humans in the environment.

However, the majority of the known systems for purifying closed areas with ozone are based on an ozone generator that utilizes a source of concentrated oxygen, for example bottled oxygen or a known pressurized oxygen generating system utilizing static discharge. When ozone is generated from a source of concentrated oxygen, the level of oxygen in the enclosure may rise along with the level of ozone. The increase in oxygen levels is due to the breakdown of ozone partially into new molecules of oxygen. An increase in the level of oxygen in enclosures containing natural perishable products enhances cellular metabolism and thus is detrimental to the storage of the perishable products.

One known method is applied to substantially closed rooms or rooms with a controlled atmosphere. The substantially closed room includes a closed circuit air conditioning system, such as a cooling system, for the preservation of perishable natural products. A known ozone generator is placed in proximity with the substantially closed room such that the ozone generator can draw in air from within the substantially closed room and liberate ozone into the substantially closed room. In contrast to other known ozonation systems, the known method utilizes oxygen from the air of the room in which the purification treatment is being applied to generate ozone. Because the method converts oxygen from the air into ozone, no increase in oxygen levels is observed in the closed room. Rather, the gaseous equilibrium is shifted so that there is maintenance of the level of oxygen in the enclosure.

The oxidative character of the ozone has a bacteriostatic and fungistatic effect in the short term, followed by a bacteriocidal and fungicidal effect. These effects combine with the lowered metabolism in a temperature cooled environment to reduce ripening, retard spoilage and thus preserve natural perishable products stored in the room.

However, the system does not provide an optimal means for efficiently sanitizing the air within the closed room.

SUMMARY OF THE INVENTION

In view of the foregoing and other exemplary problems, drawbacks, and disadvantages of the conventional methods and structures, an exemplary feature of the present invention is to provide an apparatus and method for generating reactive oxygen species and treating the air to be sanitized with the generated reactive oxygen species in order to efficiently sanitize air.

In a first exemplary, non-limiting aspect of the present invention an apparatus for sanitizing air includes a reaction unit, configured to be mounted in an air duct, for generating reactive oxygen species from oxygen in air received in the reaction unit to be sanitized.

In a second exemplary, non-limiting aspect of the present invention, a system includes an air duct, and a reaction unit disposed with the air duct.

These and other exemplary features and advantages of the present invention will become clear from the following description with reference to the accompanying drawings.

BRIEF DESCRIPTION OF THE DRAWINGS

The foregoing and other exemplary purposes, aspects and advantages will be better understood from the following detailed description of an exemplary embodiment of the invention with reference to the drawings, in which.

DETAILED DESCRIPTION OF CERTAIN EXEMPLARY EMBODIMENTS OF THE PRESENT INVENTION

Figure 1:
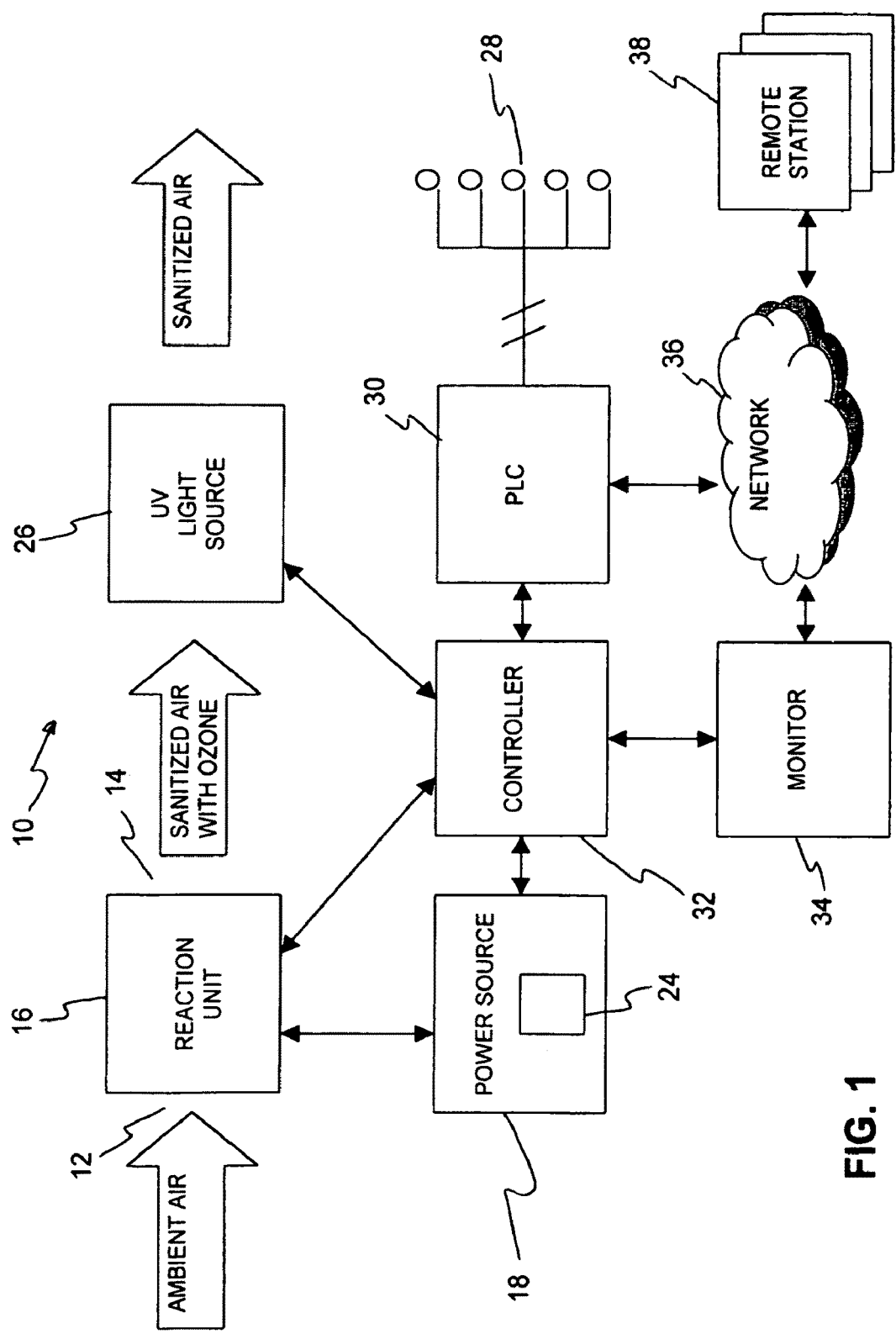
FIG. 1 illustrates a block diagram of an apparatus 10 according to an exemplary embodiment of the invention.

Referring now to the drawings, and more particularly to FIGS. 1-12, there are shown exemplary, non-limiting embodiments of the method and structures according to the present invention.

FIG. 1 shows an exemplary embodiment of the apparatus 10 for sanitizing air. The apparatus 10 includes an intake port 12 for receiving air to be sanitized and an exhaust port 14 for discharging substantially sanitized air. A reaction unit 16 is disposed between the intake port 12 and the exhaust port 14. The reaction unit 16 generates reactive oxygen species from oxygen ($O_2$) in the air received through the intake port 12.

The air received through the intake port 12 may be ambient air from the environment. The introduction of air into the reaction unit 16 may be mediated through a forced suction or by natural suction. When mediated through a forced suction, the apparatus 10 may contain a turbine, which draws air into the reaction unit 16 through the intake port 12. The air may be drawn through a filter to remove dust and other macroscopic impurities that may be present in the air to be sanitized before the air enters the reaction unit 16.

The reaction unit 16 splits the oxygen in the air into large amounts of reactive oxygen species. The reactive oxygen species generated may include singlet oxygen ($1O_2$), ozone ($O_3$), atomic oxygen (O), superoxide ($O_2$—), hydrogen peroxide ($H_2O_2$), hydroxyl radical (OH—), and peroxynitrite (ONOO—). Even though many reactive oxygen species have a short half-life, they are effective sanitizing agents. Thus, as the air passes through the reaction unit 16, a large percentage of the airborne contaminants in the air received through the intake port 12 are neutralized by the generated reactive oxygen species before the air is exhausted through the exhaust port 14. In this manner, the reactive oxygen species generated in the reaction unit 16 act as a sanitizer of the air passing through the reaction unit 16.

One of the reactive oxygen species (ROS) generated by the reaction unit 16 is ozone ($O_3$). The generated ROS is introduced into the air in the reaction unit 16, and the ROS acts as a sanitizer of the air and environment. The ROS generated in the reaction unit 16 may be discharged with the air through the exhaust port 14. The ROS in the discharged air provides the beneficial preservative effects and acts as a sanitizer for any surfaces in the environment into which the air is discharged. Other reactive oxygen species, such as hydrogen peroxide, may also be discharged with the sanitized air and have sanitizing effects similar to ozone.

The apparatus may include a power supply 18 capable of producing high frequency and high voltage output. The power supply 18 is electrically coupled with the reaction unit 16 to create a corona discharge, which splits the oxygen in the air into large amounts of reactive oxygen species. The power supply 18 provides power to the reaction unit 16.

The power supply 18 preferably includes an onboard intelligence 24, which enables the power supply 18 to adjust to changing conditions within the reaction unit 16. In this manner, the levels of reactive oxygen species generated within the reaction unit 16 can be maintained at desired levels regardless of changing conditions within the reactor unit 16. For example, the onboard intelligence 24 of the power supply 18 can compensate for variables that may affect the output of the reaction unit 16, such as changes in moisture content of the air to be sanitized or dust buildup within the reactor unit 16. The onboard intelligence 24 may be mounted on the power supply or may be a separate remote unit.

Further, the onboard intelligence 24 may allow for the dialing up and down of the levels of reactive oxygen species generated by the reaction unit 16. Preferably, the amount of reactive oxygen species generated by the reaction unit 16 is adjustable while maintaining continuous power to the reaction unit 16. However, the desired levels of reactive oxygen species may also be obtained by turning the reaction unit 16 on and off periodically. This may be achieved by using a timer or an algorithm that controls the unit's performance. Alternatively, the level of reactive oxygen species may be adjusted based on a presence or absence of contaminants in the environment to be sanitized. Furthermore, the onboard intelligence 24 may allow for the dialing up and down the levels of reactive oxygen species by changing the frequency or voltage applied to the unit 16.

The apparatus 10 may further include an ultraviolet (UV) light source 26 for illuminating the sanitized air discharged from the reaction unit 16 with UV light. By illuminating the discharged air with specific frequencies of UV light, it is possible to neutralize the ozone in the discharged sanitized air. In particular, UVB light having a frequency between about 280 nm and 290 nm will effectively neutralize the ozone. Preferably, the UV light source 26 emits UVB light having a frequency of 285 nm to achieve optimal neutralization of the ozone. In this manner, the UV light source 26 can be turned on and off as necessary to regulate the ozone levels in the air ultimately discharged into the environment while maintaining high reactive oxygen species levels within the reaction unit 16 to permit continued sanitization of the air.

Thus, by placing the UV light source 26 downstream from the exhaust port 14, the air may continue to be sanitized by the reactive oxygen species generated in the reaction unit 16, while the ozone levels of the discharged air can be selectively controlled by using the UV light source 26 to neutralize the ozone in the discharged air. The apparatus 10 may further include an adjustable arm, which can move the UV light source 26 so that it can be positioned for maximum effectiveness. The UV light source 26 may be configured using reflective surfaces in the form of a mirrored center array with concave light areas so that the UV light can be dispersed in a desired fashion, for example through the entire width of a duct, in order to maximize the ozone neutralization capability of the apparatus 10.

The apparatus 10 may further include other means for neutralizing the generated ozone. For example, the apparatus may include a heat source or carbon filtration means to neutralize the ozone in the discharged air. Additionally, a catalyst filter may be used to destroy the ozone. Additionally, the apparatus 10 may include means for neutralizing any other generated reactive oxygen species that may be discharged with the sanitized air from the reaction unit 16.

The apparatus 10 may further include a plurality of sensors and modules 28 located within the apparatus 10 and throughout the environment into which the sanitized air is discharged. The sensors and modules 28 are used to measure pertinent variables, such as ozone levels, humidity, airflow, and temperature of the air in and around the apparatus 10. A programmable logic circuit (PLC) 30 may be used to measure the performance of the apparatus 10 based on data feedback from the plurality of sensors and modules 28. The PLC 30 may store this information locally or report the information to a controller 32, which can be linked to the apparatus 10 and to a central monitor and monitoring system 34, such as a computer or other dedicated device.

In this manner, the PLC 30 may be used to monitor and control multiple functions of the apparatus 10 and facilitate data collection, retention, and reporting of performance (such as ozone output, etc.). The PLC 30 may also be used to monitor and control the power supply 16 through the onboard intelligence 24. Thus, the onboard intelligence 24 may use the feedback from the sensors and modules 28 to appropriately adjust the reaction unit 16 to provide the desired levels of reactive oxygen species.

The PLC 30 may be appropriately configured to make the information accessible to a remote computing device 38 over a network 36. The network 36 may include any known communications or networking means, for example, a Wide Area Network (WAN), Local Area Network (LAN), Internet, Bluetooth®, or any wireless connection. Thus, the PLC 30 may permit regulation and diagnosis of the apparatus 10 remotely by the computing device 38 over the networking means 36. It is to be understood that one or more of the onboard intelligence 24, PLC 30, controller 32, and monitoring system 34, or functions thereof, may be provided on a single appropriately configured computing device for monitoring and controlling the functions of the apparatus 10.

Figure 2:
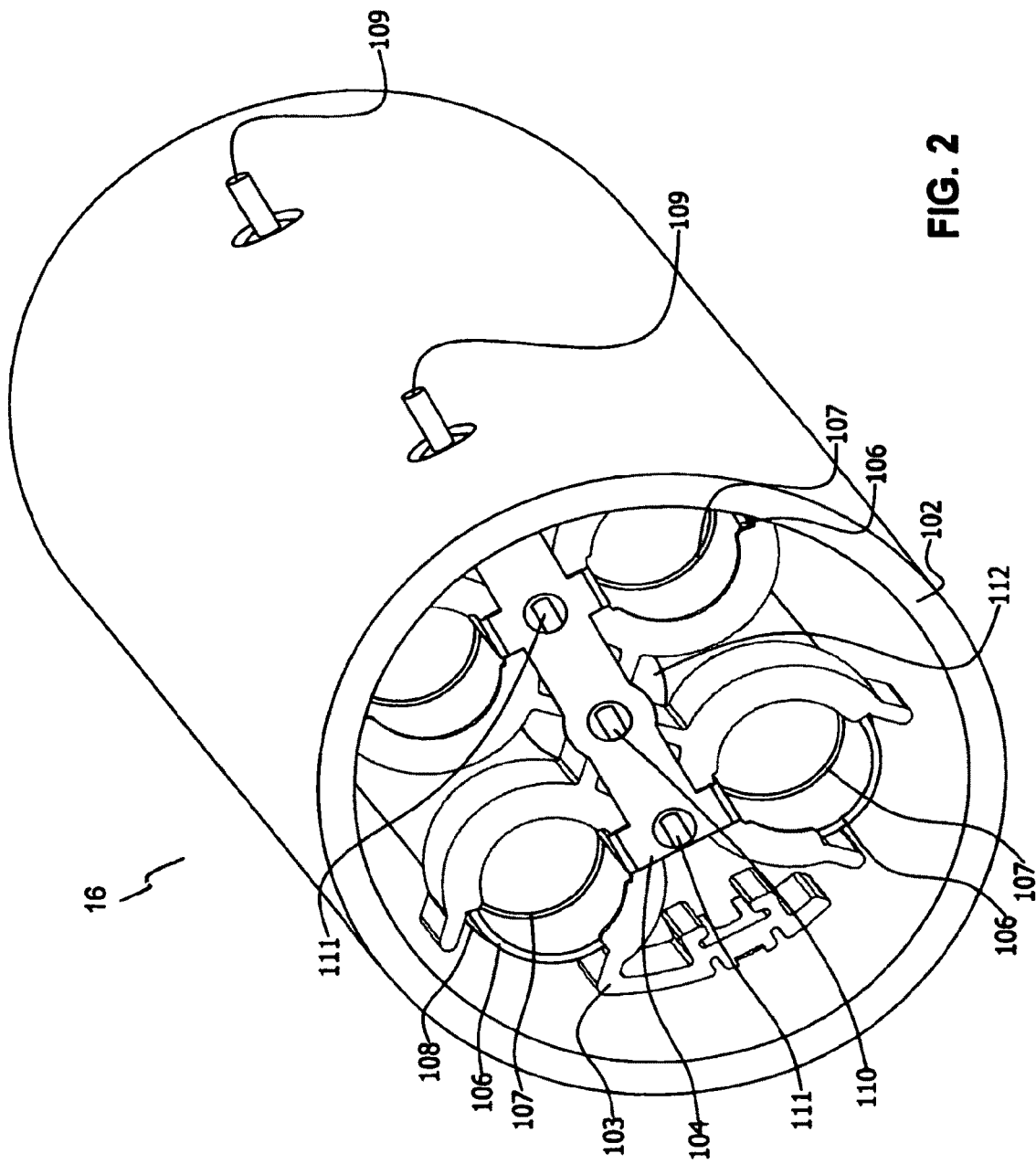
FIG. 2 illustrates a perspective view of a reaction unit 16 according to an exemplary embodiment of the invention.
Figure 3:
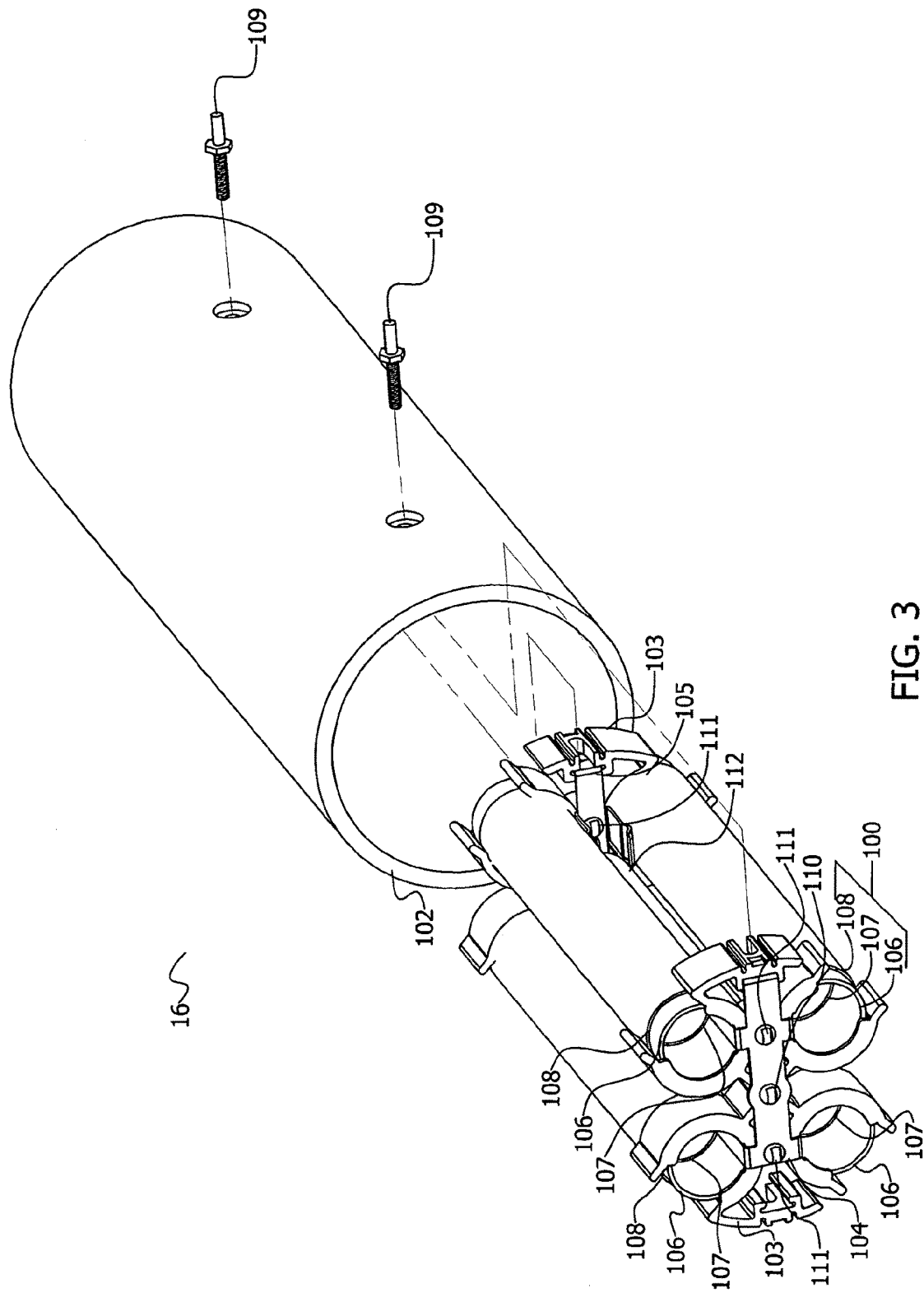
FIG. 3 illustrates an exploded perspective view of the reaction unit 16 illustrated in FIG. 2.
Figure 4:
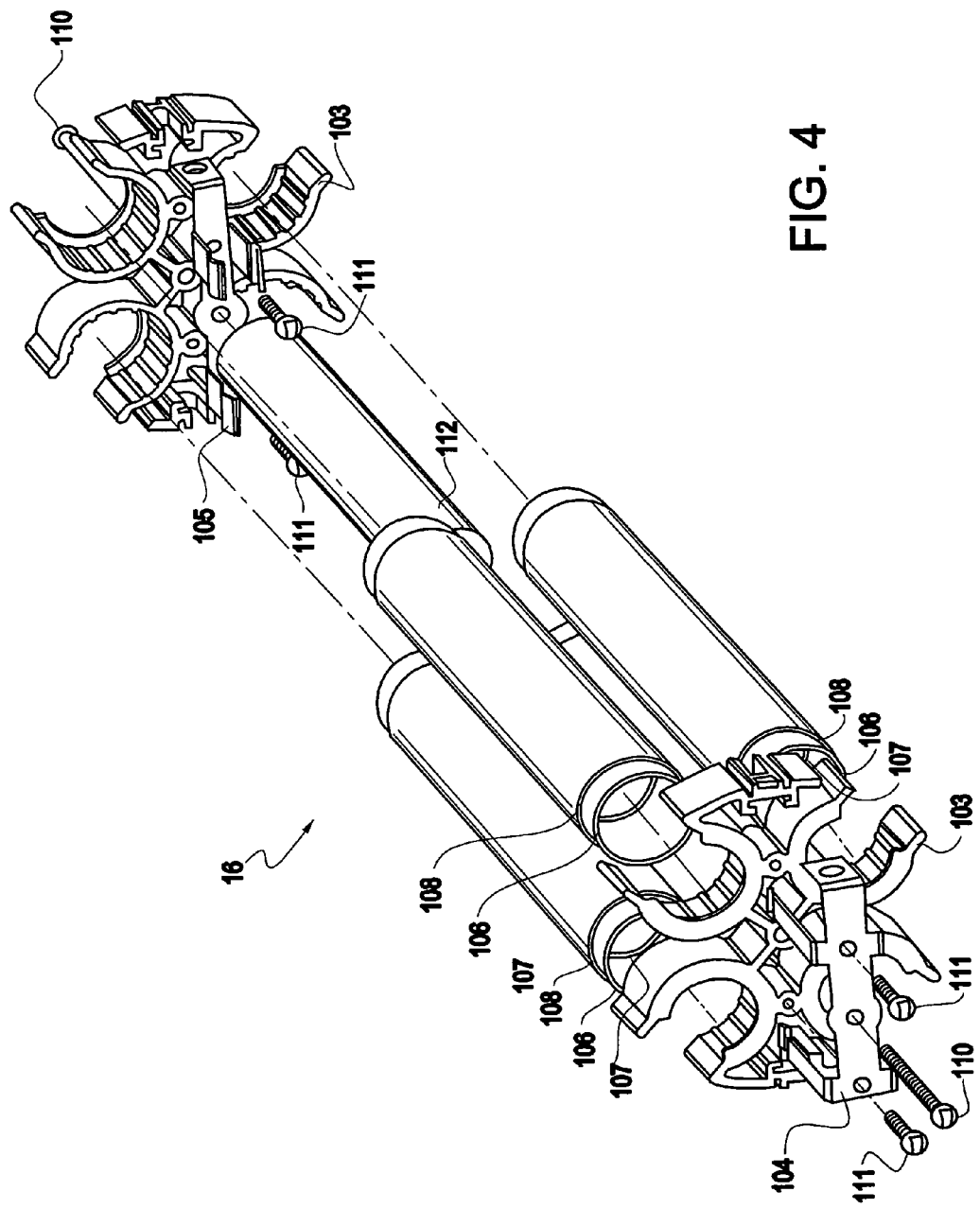
FIG. 4 illustrates a further exploded perspective view of the reaction unit 16 illustrated in FIG. 2.

FIGS. 2-4 illustrate perspective and exploded views of an exemplary embodiment of the reaction unit 16 of the invention. The reaction unit 16 may include one or more reaction chambers 100 in which the reactive oxygen species are generated. The reaction chambers 100 may be arranged in an array within a housing 102. The housing 102 may consist of round polyvinyl chloride (PVC) pipe of appropriate size. However, it is understood that the housing may be of any desired shape or material. For example, the housing 102 may consist of the duct work of an HVAC system.

Preferably, the reaction chambers 100 are held in place within the array by a coupler arranged on both ends of the reaction chambers 100. The coupler may include a clamp 103 for securing the reaction chambers 100 in a desired location within the array. A center support rod 112 may be included in the array and appropriately secured by the clamp 103 to provide additional structural integrity to the array. The coupler may further include an electrically conductive contact 104,105 cooperatively shaped with the clamp 103 and contacting each of the reaction chambers 100 within the array. The contact 104 may be integrally formed with the clamp 103 or mechanically attached to the clamp 103 by adhesive or mechanical fasteners 111.

The coupler preferably cooperates with an inner surface of the housing 102 to secure the reaction chambers 100 within the housing 102. The array may be fixed within the housing 102 using contact studs 109. The electrically conductive contact studs 109 pass through the housing 102 and interact with the coupler so as to fixedly secure the clamp 103 in relation to the housing 102 and electrically connect with the contacts 104,105. In this manner, any electrical connections between the reaction chamber 100 of the reaction unit 16 and the power supply 18 may be achieved through the contact studs 109. However, the electrical connections may be achieved by other means.

Figure 5:
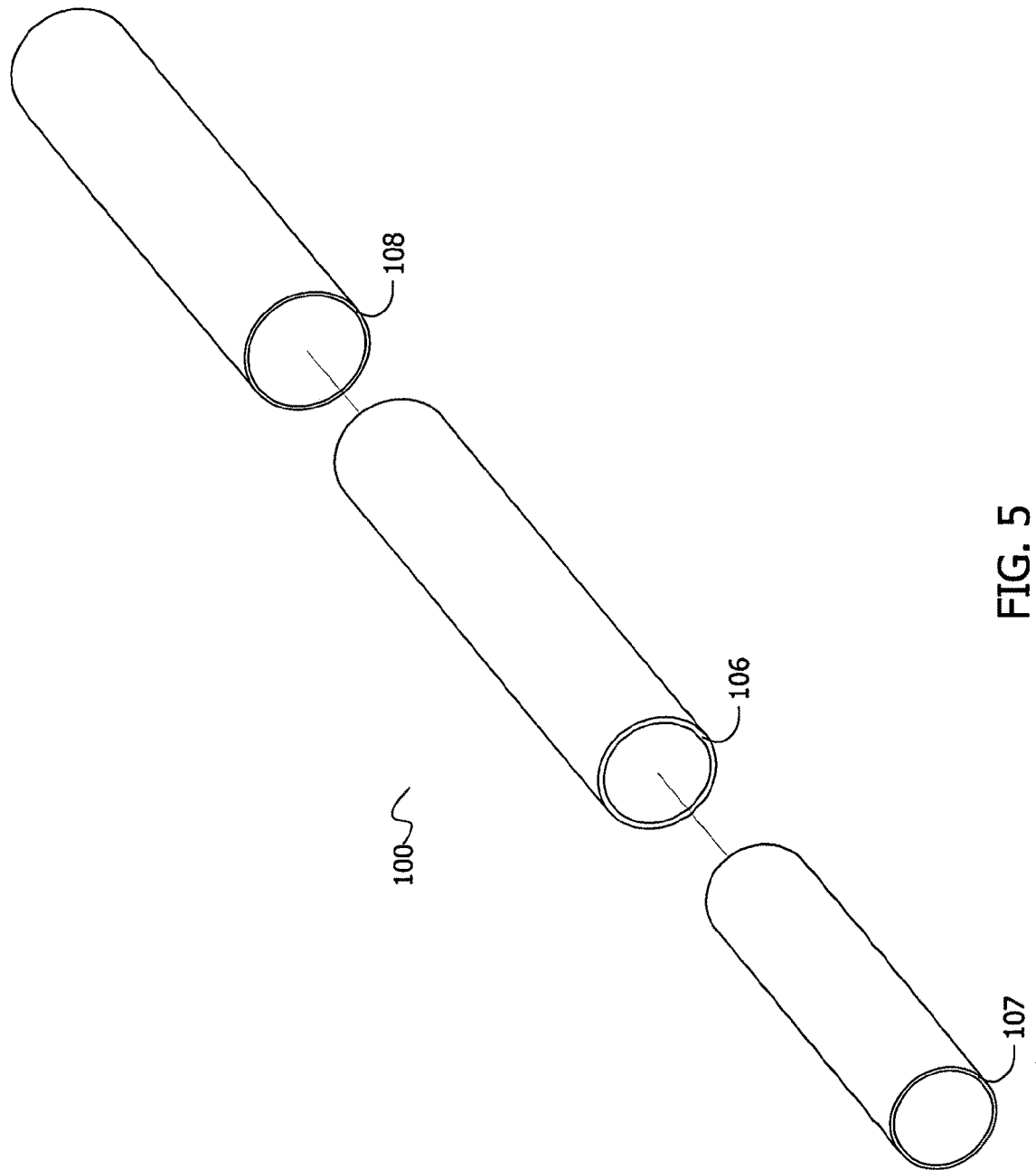
FIG. 5 illustrates an exploded perspective view of a reaction chamber in accordance with an exemplary embodiment of the present invention.

As shown in FIG. 5, the reaction chamber 100 may consist of a glass tube 106 lined with an inner stainless steel mesh 107 and wrapped in an outer stainless steel mesh 108. This configuration has been found to create a very effective corona that is able to generate a large amount of reactive oxygen species without using a static discharge and without producing material amounts of off gases, such as nitrous oxide. While a round configuration for the reaction chamber is shown, the reaction chambers for generating reactive oxygen species may include different configurations and materials. For example, the reaction chambers may be formed of a glass tube 106 wrapped in stainless steel mesh with a copper tube coated with gold inside the glass tube at specific gaps. The reaction chambers may also be formed using appropriately configured plates of glass, ceramic or other materials with metal mesh on opposite sides. The particular configuration may be chosen to comport with the desired application of the apparatus 10.

Figure 6:
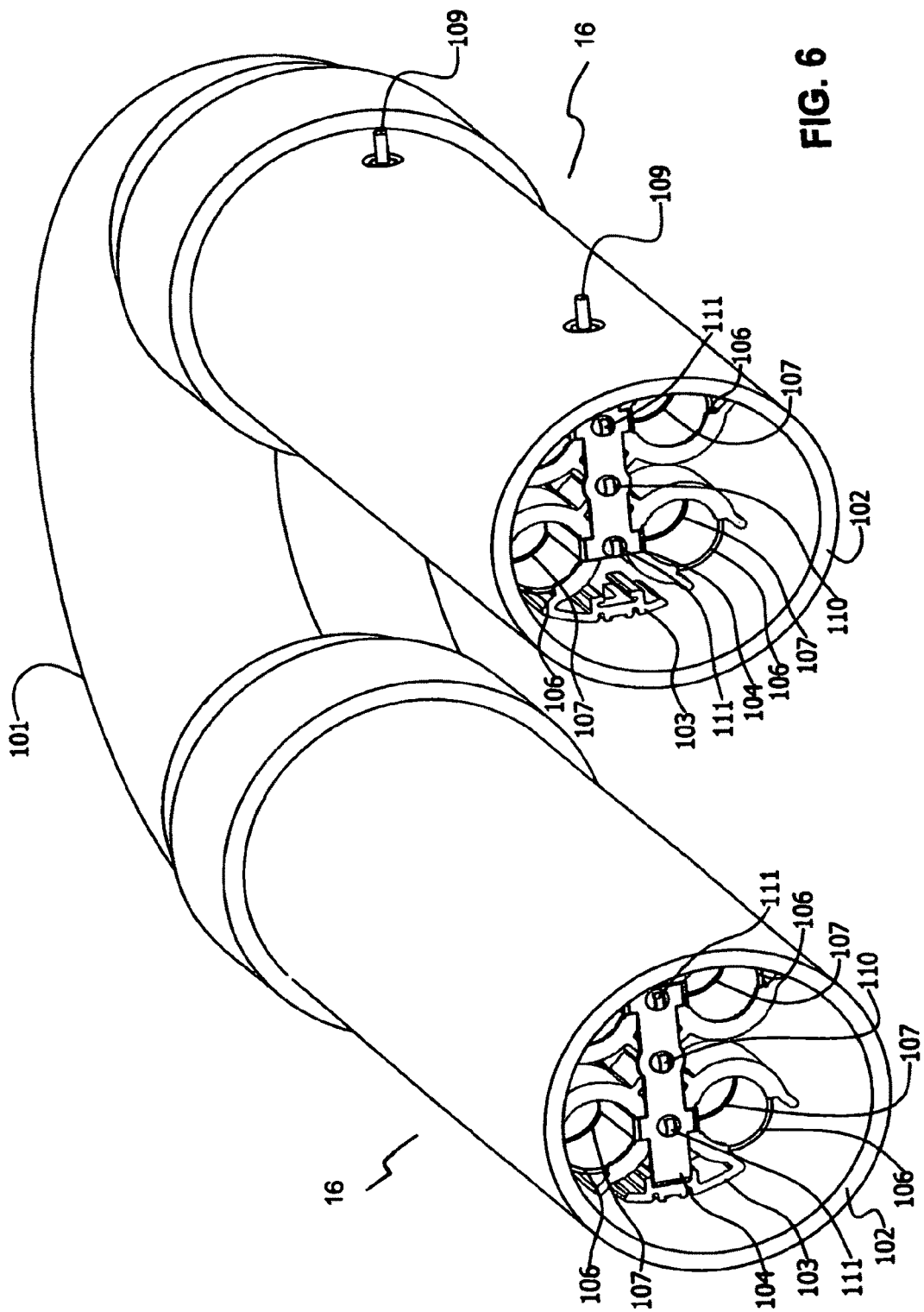
FIG. 6 illustrates a perspective view of a reaction unit in accordance with another exemplary embodiment of the present invention.

As shown in FIG. 6, the apparatus 10 may include a plurality of reaction units 16 fluidly linked in a serial manner. In this manner, the air to be sanitized may be passed through multiple reaction units 16 in order to maximize the exposure of air to the reactive oxygen species, therefore greatly increasing the effective sanitation of the air. While a U-shape is shown, the reaction units 16 may be arranged in any manner depending on the space constraints of the desired application of the apparatus 10.

The reaction units 16 may be linked using an appropriate connector 101 that links the housings 102 of the reaction units 16. The reaction units 16 may be linked using a butt-plate. The butt-plate may include all the necessary electrical connections for the reaction units 16 to eliminate high-voltage wiring and avoid wiring problems. This also makes servicing the apparatus 10 more streamlined and efficient. The electrical connections between the reaction units 16 may be achieved using military lock in rotation connectors connecting the butt-plate 24 and reaction units 16. Additionally, each reaction unit 16 may have its own power supply 18 in order to make the apparatus 10 highly scalable.

The apparatus 10 may be configured for general room sanitization applications where the apparatus 10, or components thereof, may be placed in the duct work of an HVAC system servicing the room to be sanitized. Alternatively, the apparatus 10 may be incorporated into the HVAC system of a facility to generally sanitize the air in the facility. Additionally, the apparatus 10 may be used to sanitize air to be introduced to a room from an outside source (make up air), as well as to treat exhaust air to remove smells and contaminants before releasing the air into the environment.

The apparatus 10 may be placed directly into a duct of an HVAC system so that some of the components are external to the duct in order to balance or reduce the weight of the apparatus 10 and create less stress on the duct work. For example, one or more reaction units 16 may be placed in the duct so that the air in the duct flows directly through the reaction unit 16 resulting in the generated reactive oxygen species sanitizing the air passing through, and the generated reactive oxygen species cleaning the duct and being dispersed into the environment. As described above, a UV light source 26 may be placed downstream from the reaction units 16 in the duct to regulate the dispersion of ozone into the environment.

The level of ozone maintained in the environment into which the sanitized air containing reactive oxygen species is dispersed, for example a room or building might vary from as low as 0.01 PPM (or even as low as mere trace amounts) to higher levels depending on regulations and safe operating conditions based on human presence. The optimum level will be determined based on the size, configuration, and contents of the room. Further, the levels of reactive oxygen species maintained in the environment used by people may be limited by governmental regulation. For example, OSHA regulations stipulate that eight hours of exposure to 0.1 PPM ozone is acceptable and that fifteen minutes of exposure to 0.3 PPM ozone is acceptable. Use of higher concentrations may be dangerous. According to certain exemplary embodiments of the present invention, the level of ozone will be controlled and maintained, for example by the PLC 30, in accordance with governmental regulations. Higher levels of reactive oxygen species may be used during unoccupied periods for additional sanitation.

While the description refers to sanitizing air to be discharged into a room, space, or environment, it is to be understood that the invention can be applied to any defined environment. For example, an environment may be defined by solid surfaces or barriers, such as walls or product packaging, or defined by streams of forced gases, such as air screens or air curtains. Alternatively, the environment may be simply defined by the specific requirements of a desired application of the invention.

An exemplary application of the apparatus 10 would be for sanitizing sensitive areas of medical facilities, such as acute care areas and operating rooms. For example, the air circulation system of an operating room may include a network of ducts and vents that allow for the circulating of the air within the room without taking in air from outside the room. The apparatus 10, or elements thereof, may be placed in the duct work so that the air in the operating room may circulate through one or more reaction units 16. By including a UV light source 26, when the room is in use, the UV light source 26 may be turned on to prevent ozone from being dispersed in the room. When the room is not occupied, however, the UV light source 26 may be turned off, allowing the generated ozone to circulate throughout the room and remove contaminants from surfaces inside the room. Similarly, a catalyst filter may be used. It is to be understood that the apparatus 10 may be employed in a wide variety of medical applications. For example, the sterilization of medical equipment storage cabinets and rooms, such as endoscope cabinets, and the sanitization of other rooms of medical facilities, such as waiting rooms, bathrooms, and food production areas.

In a similar manner, the apparatus 10 may be utilized in food processing environments to sanitize the air while food is being processed with workers present, provide the beneficial preservative effects of ozone while food is being stored (before and after processing), and sanitize the air and surfaces while the processing room is vacant. The apparatus 10 may also be configured into food processing equipment so that food is treated as it moves through the equipment, for example on a conveyor belt, automatic cutters and slicers and inspection areas. The product may be tumbled to promote uniform treatment. The apparatus 10 may also be configured to be placed in containers, trailers, and rail cars or as a component to a refrigeration system of such containers, trailers, and rail cars to sanitize the air therein while providing the beneficial preservative effects of ozone to any products stored therein.

Other exemplary applications of the apparatus include the provision or incorporation of the apparatus 10 into: grocery store display cases, such as deli counters and meat, fish and poultry display cases; floral display cases, both refrigerated and non-refrigerated; and HVAC systems of various public transportation means, such as cars, buses, trains, subways, or aircraft. The invention may be employed in pressurized environments, such as aircraft and positively or negatively pressurized rooms and structures. The apparatus 10 may also be incorporated into packing and production line equipment that blows air into bags as products are packed and sealed to sanitize the air blown into the bag and preserve the product therein, or into equipment that is integrated into a production line to sanitize the air and product before packaging.

As noted above, the apparatus 10 may also be incorporated into the HVAC system of public buildings in order to generally treat the air within the buildings. In this manner, the apparatus 10 may be used to sanitize the air and eliminate odors in the buildings. For example, office buildings, restaurants, malls, hospitals, and the like would be particularly appropriate applications due to the large numbers of people that occupy the buildings and the need to sanitize the air in the buildings to provide a healthier, cleaner and more desirable environment for the occupants. The apparatus 10 may further be employed to sanitize air that is to be exhausted out of buildings in order to eliminate or reduce contaminants and odors emitted from the building into the surrounding environment.

In another exemplary application of the invention, the apparatus 10 may include sensors 28 for detecting potentially harmful agents in the environment. For example, the apparatus 10 may be incorporated into an HVAC system of a building and include appropriate sensors 28 for detecting noxious chemical or biological agents that may be unlawfully or accidentally released in or around the building. The apparatus 10 may be appropriately controlled to automatically operate in response to a positive detection of such agents by the sensor 28 in order to sanitize the air and protect the occupants of the building from the harmful agents.

In yet another application of the invention, the sanitized air discharged into the environment may be directed through a nozzle or jet to permit directional control of the sanitized air. In this manner, the sanitized air can be actively directed to a specific location or area requiring the sanitizing effect of the discharged air. Similarly, the invention may be incorporated into a means for creating air curtains or air doors. For example, an air curtain can be created to substantially enclose a specified space in order to contain and control any undesirable odors or emissions from contents within the created space, or, alternatively, sanitize or preserve the contents within the created space.

In a further exemplary application of the invention, the apparatus 10 may be incorporated into vacuum cleaner devices, for example stand-alone or centralized vacuum cleaners, wet-dry vacuums, and carpet cleaners, in order to sanitize air discharged from the cleaner. In this manner, any contaminants and odors inhaled by the cleaner would be sanitized and not discharged into the environment in which the cleaner was being utilized.

Figure 7:
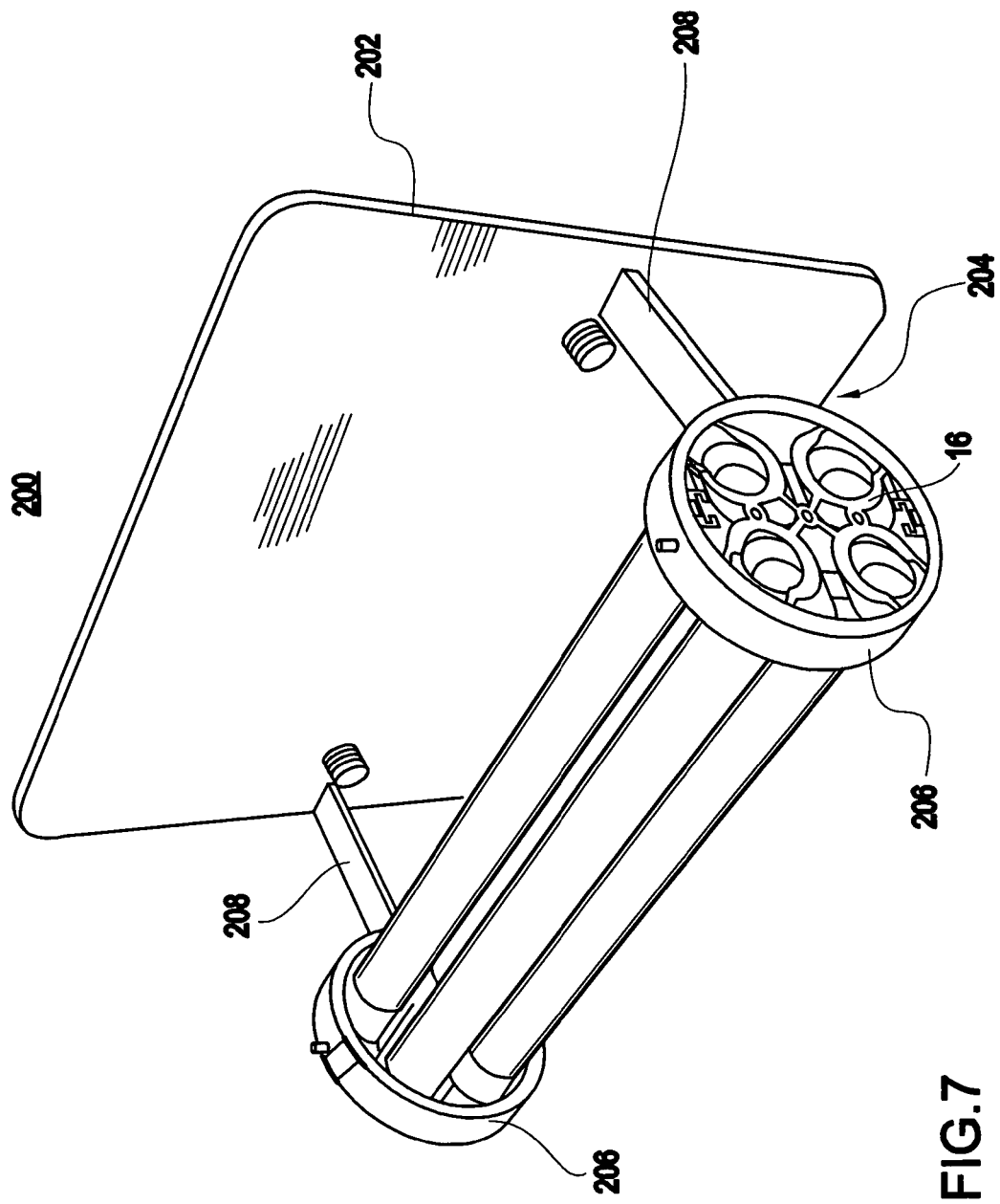
FIG. 7 illustrates an in-duct apparatus 200 according to an exemplary embodiment of the present invention.

As mentioned above, the apparatus 10 may be incorporated into an air duct system (e.g., a HVAC system of a building). FIG. 7 illustrates such an in-duct unit 200 according to an exemplary embodiment of the present invention.

The in-duct unit 200 is configured to mount a reaction unit 16 within an air duct. The in-duct unit 200 includes a duct mounting plate 202 and a reaction unit support system 204. The reaction unit support system 204 includes a generally circular support member 206 at each end of the reaction unit 16 and a mounting arm/bracket 208 extending from each circular support member 206. The mounting arms/brackets 208 are configured to secure the reaction support system 204 to the mounting plate 202. According to the exemplary embodiment of the invention illustrated in FIG. 7, the mounting arms 208 are secured to the mounting plate 202 by screws.

Furthermore, the in-duct unit 200 includes wire glands 210. The wire glands 210 are disposed on the mounting plate 202 adjacent each of the mounting arms 208. The wire glands 210 include apertures through which wires can reach the reaction unit 16 from a control unit.

Figure 8:
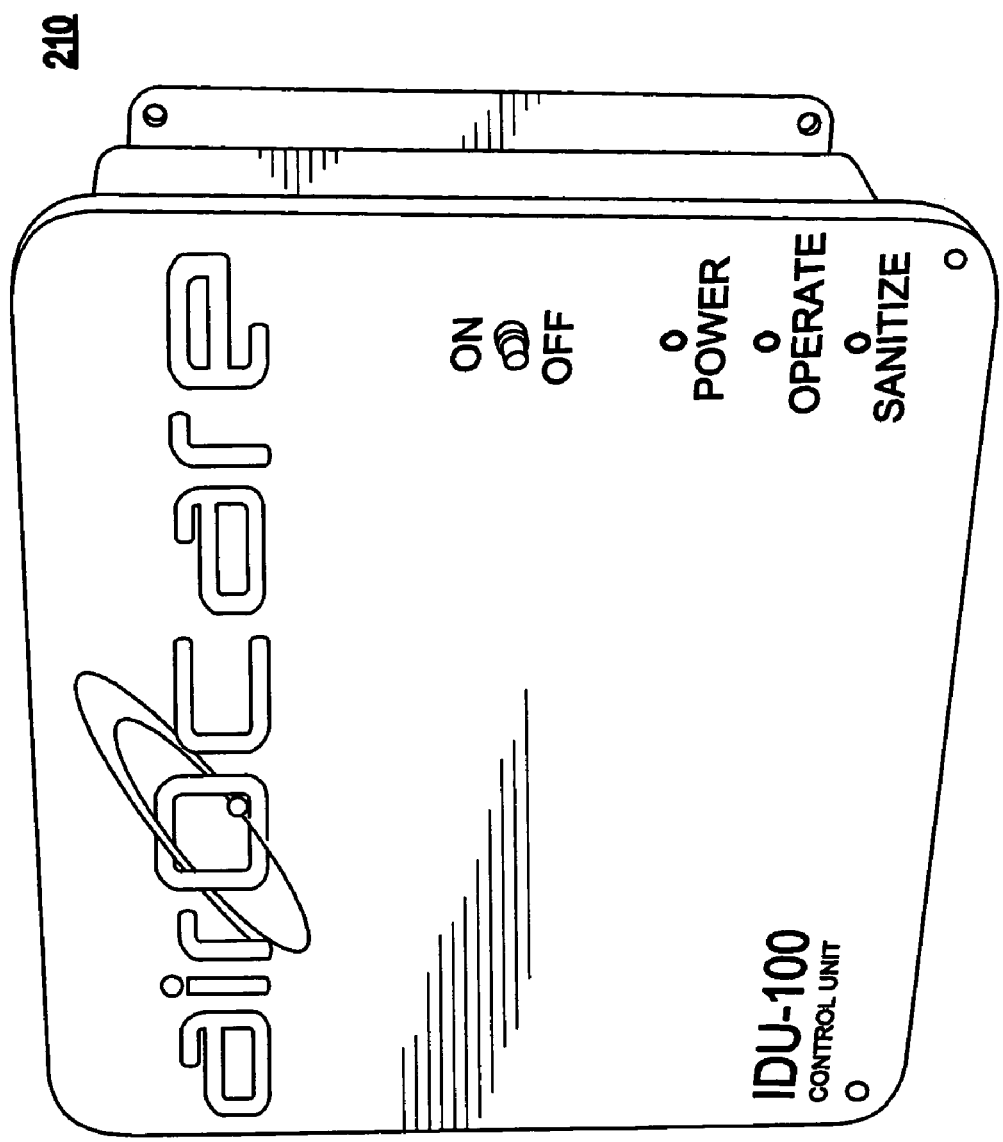
FIG. 8 illustrates a control unit 210 of the in-duct apparatus 200 illustrated in FIG. 7.

FIG. 8 illustrates a control unit 210 of the in-duct apparatus 200 illustrated in FIG. 7. The control unit 210 houses a subsystem of the in-duct apparatus. The control unit 210 controls the in-duct unit and provides power to the reaction unit 16. The control 210 may be mounted on an exterior of the air duct or may be provided as a remote unit.

Figure 9:
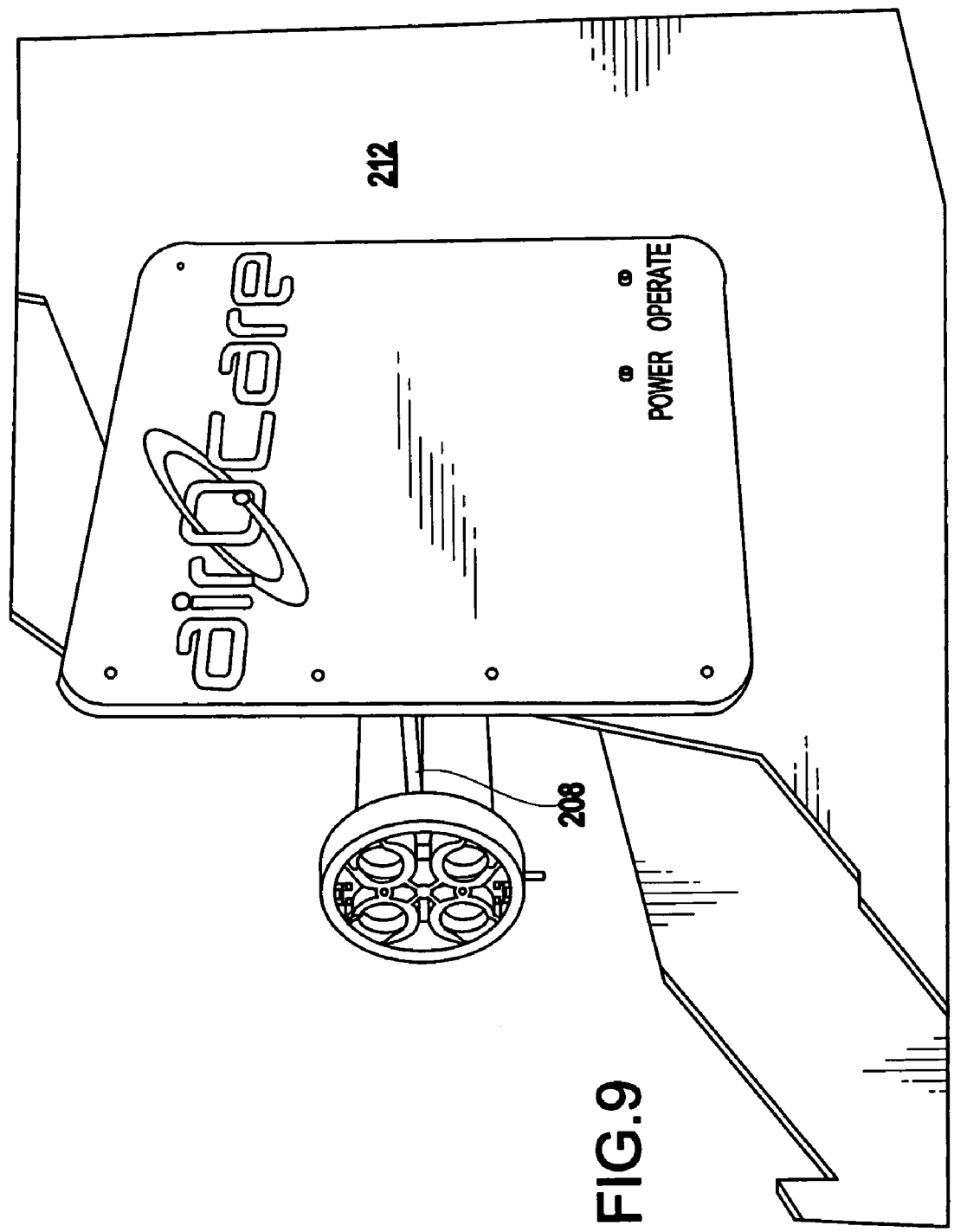
FIG. 9 illustrates an external view of an air duct in which the in-duct apparatus 200, illustrated in FIG. 7, is mounted.
Figure 10:
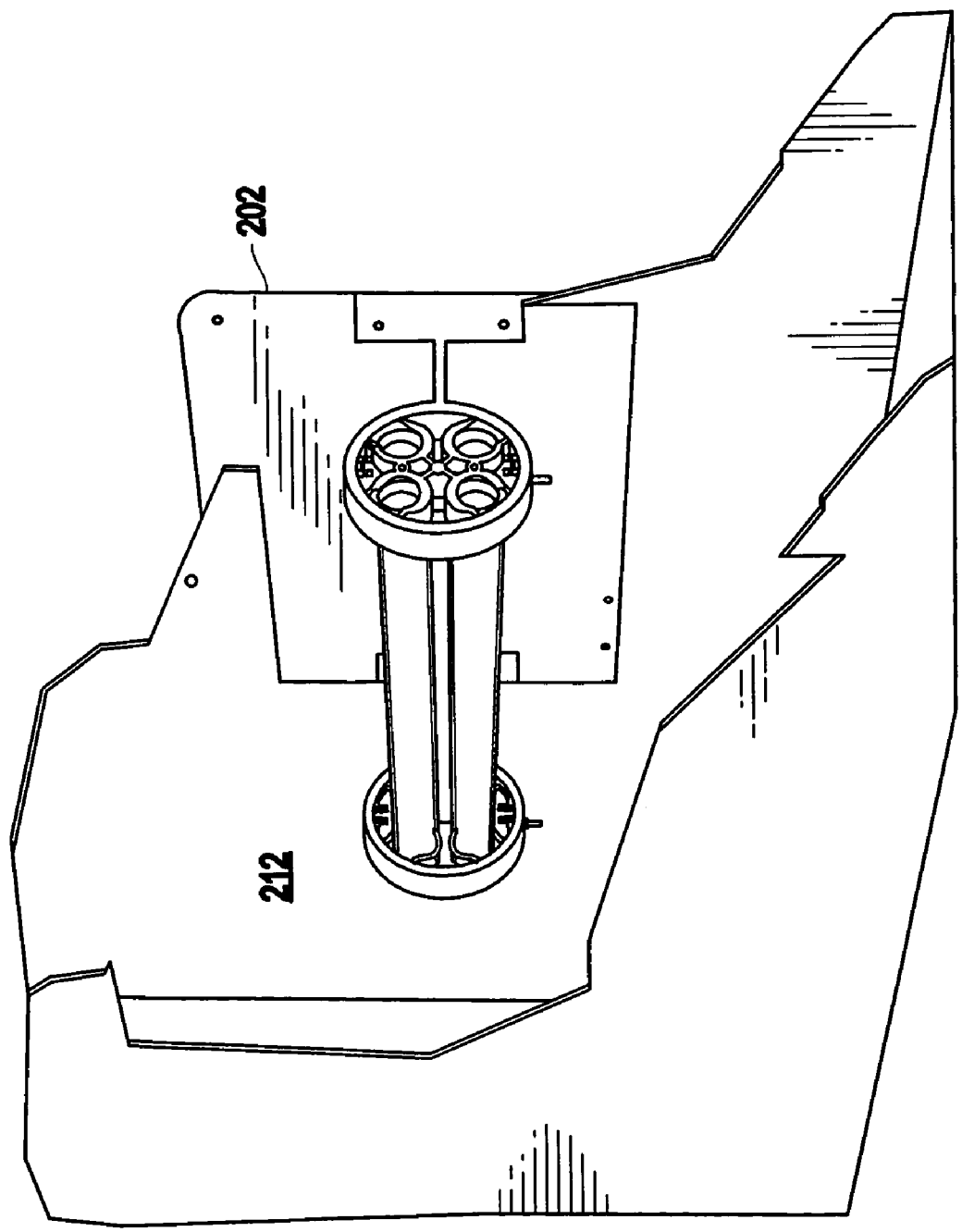
FIG. 10 illustrates an internal view of the air duct illustrated in FIG. 9.

FIG. 9 illustrates an external view of the in-duct apparatus 200 mounted in an air duct 212. FIG. 10 illustrates an internal view of the in-duct apparatus 200 mounted in an air duct 212. According to an exemplary embodiment of the present invention, the mounting plate 202 is mounted on an exterior wall of the air duct 212. The mounting arms 208 mount the reaction unit 16 to the mounting plate 202 through the wall of the air duct 212. Alternatively, the mounting plate 202 may be mounted along an interior wall of the air duct 212.

The in-duct unit is designed to treat air within an air duct. The reaction unit 16 in the in-duct unit 200 does not require a turbine, as the reaction unit 16 relies on airflow within the air duct.

The in-duct unit 200 is powered by 110 Volts AC and consumes very little power. This is achieved using a 12 VDC reactor power array. The power array consists of a plurality of (e.g., two) 12 VDC power supplies.

Figure 11:
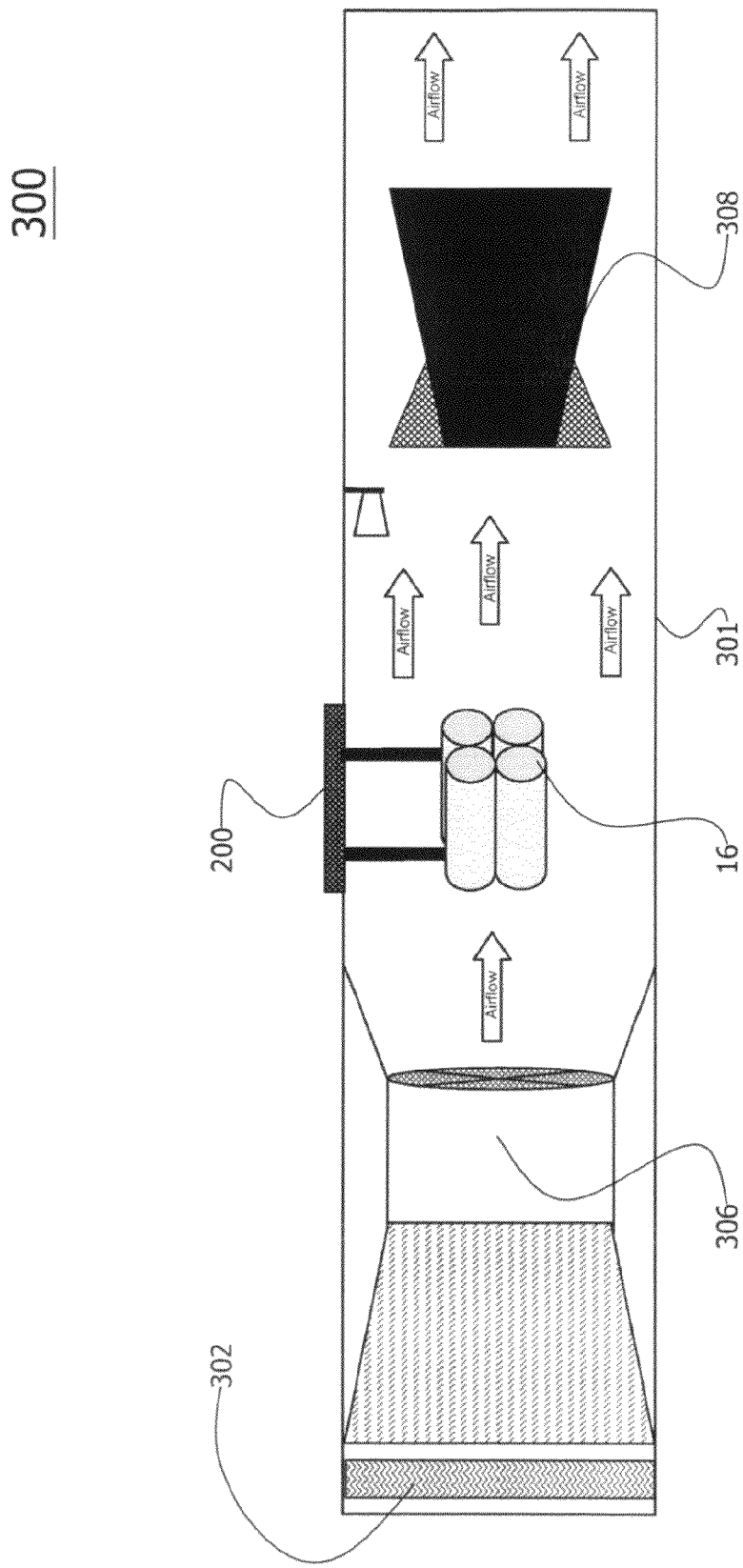
FIG. 11 illustrates a system 300, including the in-duct apparatus 200, according to an exemplary embodiment of the present invention.

FIG. 11 illustrates an air duct system 300 according to certain exemplary embodiments of the present invention. The system 300 includes an air duct 301 with an air flow through the air duct (see air flow arrows in FIG. 11).

The in-duct unit 200, including the reaction unit 16, is mounted within the air duct 301, as described above. The system may include one or more fans (e.g., HVAC fans) 302,306 at a first end of the air duct and a vortex 308 positioned at a second end of the air duct 308. The reaction unit 16 is mounted between the fans 302, 306 and the vortex 308. The vortex 308 is configured to mix an output from the reaction unit with air in the air duct.

Figure 12:
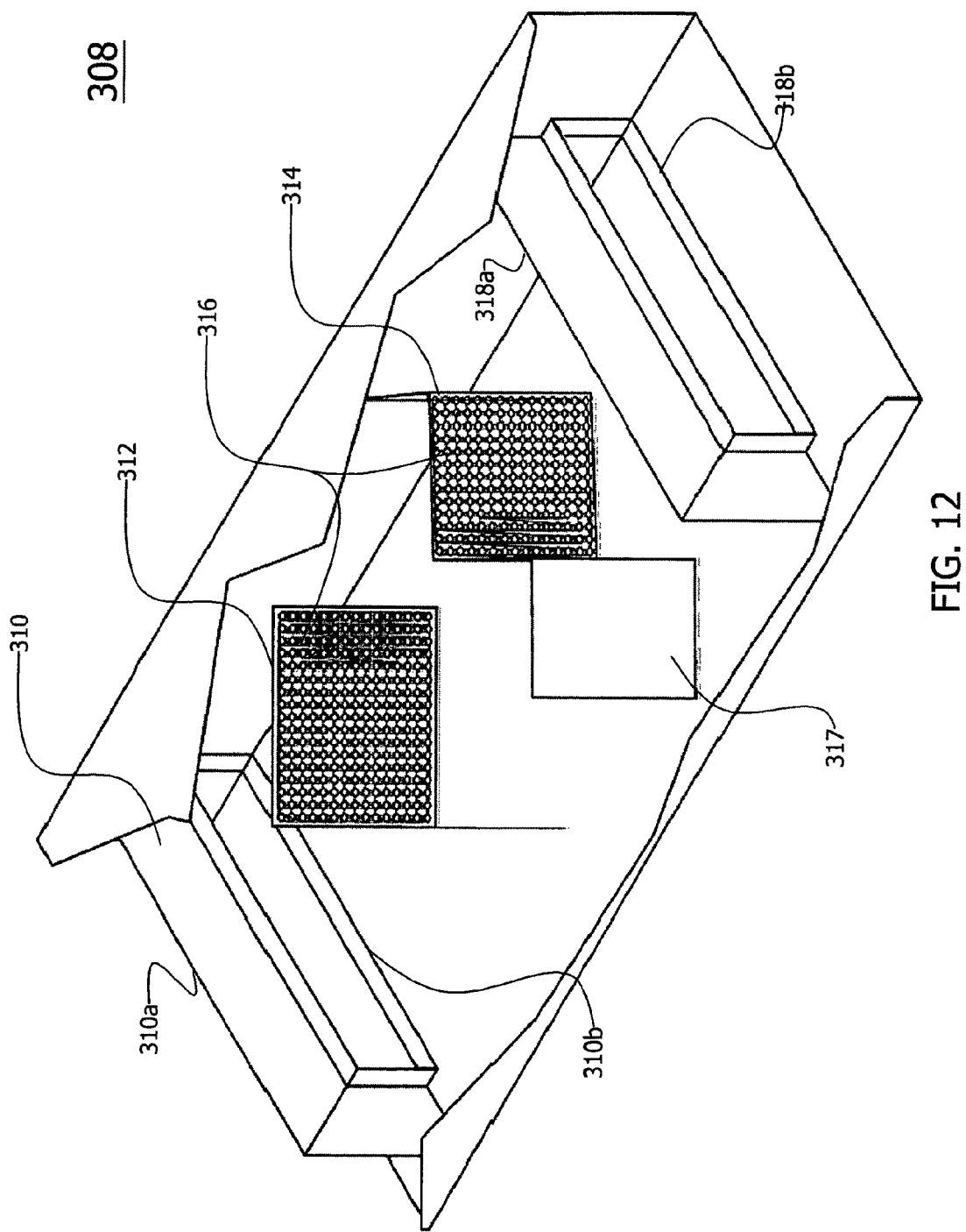
FIG. 12 illustrates an internal view of a vortex of the system 300 illustrated in FIG. 11.

FIG. 12 illustrates an interior view of the vortex 308. The vortex 308 mixes the reactive oxygen species emitted from the reaction unit 16 and controls the airflow after the fan.

The vortex 308 includes an input opening 310. The input opening 310 is configured to increase the airflow speed entering the vortex 308. The increased airflow speed helps to mix the reactive oxygen species with the air flowing through the air duct. As is illustrated in FIG. 12, the air enters into the vortex through an exterior portion 310a of the input opening and exits the input opening 310 into the body of the vortex through an interior portion 310b. The interior portion 310b is smaller than the exterior portion 310a in both height and width. Furthermore, the body of the opening 310 between the exterior portion 310a and the interior portion 310b is tapered. This shape of the input opening 310 causes the airflow speed entering the vortex 308 to increase. That is, since the opening 310 in the vortex 308 is smaller than the air duct, the vortex 308 produces a tunnel effect, which increases the speed of the airflow.

The vortex 308 also includes an output opening 318 positioned at an output end of the vortex 308. The output opening 318 is substantially the same size as the input opening 310 and is configured to increase the airflow speed. Accordingly, the internal pressure within the air duct is balanced.

The air traveling through the vortex passes through an interior portion 318a of the output opening and exits the input opening 318 through an exterior portion 318b. The exterior portion 318b is smaller than the interior portion 318a in both height and width. This shape of the input opening 310 causes the airflow speed entering the vortex 308 to increase.

The vortex 308 includes one or more plates disposed between the input opening 310 and the output opening 318. In the exemplary embodiment illustrated in FIG. 12, the vortex includes a first row of plates 312 and a second row of plates 314.

The first row of plates 312 includes a plurality of airflow mixing plates 316. The airflow mixing plates are disposed at an angle to create a v-shape member, as is illustrated in FIG. 12. The airflow mixing plates 316 are perforated to allow air to flow through them at a compressed rate. The rate of the air flow is compressed due to the size of the holes in the airflow mixing plates 316.

The second row of plates 314 includes a combination of airflow mixing plates 316, described above, and back flow plates 317. The plates in the second row plates 314 are position in an alternating angled arrangement with the airflow mixing plates 316 position in a center of the second row of plates 314 and the back flow plates 317 positioned at ends of the second row of plates 314.

The back flow plates 317 are not perforated. The back flow plates 317 are configured to create backflow, which helps to mix the reactive oxygen species in the airflow.

In accordance with certain exemplary embodiments of the present invention, the entire vortex is made of metal. Specifically, the entire vortex may be made of 26 gauge galvanized metal.

According to certain exemplary embodiments of the present invention, the reaction unit 16 may be provided as a complete system or may be easily mounted within an existing air duct system.

While the invention has been described in terms of several exemplary embodiments, those skilled in the art will recognize that the invention can be practiced with modification within the spirit and scope of the appended claims.

Further, it is noted that, Applicants' intent is to encompass equivalents of all claim elements, even if amended later during prosecution.

What is claimed is:

1. A system, comprising:
   an air duct;
   a reaction unit disposed within the air duct, said reaction unit configured to generate ozone and reactive oxygen species from oxygen in air received in the reaction unit to be sanitized; and
   a vortex disposed downstream from and spaced apart from an output end of said reaction unit, said vortex configured to mix an output from said reaction unit with air in the air duct, said vortex comprising:
   an input opening, configured to increase airflow speed entering said vortex, said input opening comprising:
   an exterior portion, configured to receive air entering said vortex;
   an interior portion, said interior portion having a height and a width each smaller than a height and a width of the exterior portion; and
   a tapered body portion disposed between the exterior portion and the interior portion;
   an output opening, configured to increase airflow speed exiting said vortex, said output opening comprising:
   an interior portion;

an exterior portion configured to release air from said vortex, said exterior portion having a height and a width each smaller than a height and a width of the interior portion; and a tapered body portion disposed between the exterior portion and the interior portion;

a first row of plates disposed between said input opening and said output opening, said first row of plates comprising a plurality of perforated airflow mixing plates disposed at an angle such that said plurality of perforated airflow mixing plates create a V-shaped member; and a second row of plates disposed downstream from said first row of plates, said second row of plates comprising:

a plurality of perforated airflow mixing plates; and a plurality of solid back flow plates, wherein said second of plates are positioned in an alternating angled arrangement with said plurality of perforated airflow mixing plates positioned in a center of said second row of plates and said plurality of solid back flow plates positioned at ends of the second row of plates.

2. The system according to claim 1, further comprising a mounting unit configured to mount the reaction unit in the air duct, said mounting unit comprising:

a reaction unit support system disposed around an exterior of the reaction unit;

a pair of mounting arms, each arm extended from an end of the reaction support system; and a mounting plate, the pair of mounting arms being secured to the mounting plate, disposed along an exterior of the air duct.

3. The system according to claim 1, wherein the reactive oxygen species generated comprise at least one of singlet oxygen, superoxide, hydroxyl radical, and peroxynitrite.

4. The system according to claim 3, further comprising an ultraviolet light source positioned downstream from an exhaust of said reaction unit.

* * * * *